United States Patent [19]

Lincoff

[11] Patent Number: 5,207,660

[45] Date of Patent: May 4, 1993

[54] METHOD FOR THE DELIVERY OF COMPOSITIONS TO THE OCULAR TISSUES

[75] Inventor: Harvey A. Lincoff, New York, N.Y.

[73] Assignee: Cornell Research Foundation, Inc., Ithaca, N.Y.

[21] Appl. No.: 691,836

[22] Filed: Apr. 26, 1991

[51] Int. Cl.$^5$ ............................................. A61M 35/00
[52] U.S. Cl. ..................................... 604/300; 604/294
[58] Field of Search ................. 514/170; 604/300, 294

[56] References Cited

U.S. PATENT DOCUMENTS

| | | | |
|---|---|---|---|
| 3,788,327 | 1/1974 | Donowitz et al. | 128/350 R |
| 3,954,110 | 5/1976 | Hutchison . | |
| 4,299,227 | 11/1981 | Lincoff | 128/344 |
| 4,454,151 | 6/1984 | Waterbury | 424/274 |
| 4,820,270 | 4/1989 | Hardcastle et al. | 604/96 |

OTHER PUBLICATIONS

Clinical Ophthalmology, vol. 4, Chap. 43, "Nonspecific Treatment of Uveitis" T. F. Schlaegel, Jr., pp. 1-13, (1988).
Arch Ophthal–Vol. 83, May 1970, "Orbital Infusion of Steroids in the Rabbit", Norman D. Levine et al., pp. 599-607.
Reprinted from Ophthalmology, American Academy of Ophthalmology, Apr. 1979, "A Temporary Balloon Buckle for the Treatment of Small Retinal Detachments", Harvey A. Lincoff, et al., pp. 586-592.
Arch Ophthalmol–Vol. 108, Apr. 1990, "A Fiberoptic Stylette for Localizing the Balloon Buckle" Harvey Lincoff, et al., p. 607.
Dept. of Ophthalmol, School of Med., Tottori Univ. 86, 75, Dexamethasone, "Studies on the Intraocular Penetration of Dexamethasone after Subcojunctivel or Retrobulbar Injection in Rabbits", N. Ichigashira, pp. 1453, 1455, 1457, 1459 and 1460.
Am. Journal of Ophthalmology, vol. 62, No. 4, Oct. 1966, "Restoration of Vision in Temporal Arteritis by Retrobulbar Injections of Steroids", Robert A. Schimek, et al., pp. 693-696.
J. Neurosurg. 63:806-810, 1985, "Current application of 'high-dose' Steroid Therapy for CNS Injury—A pharmacological perspective", J. Mark Braughler, et al.
Am. Journal of Ophthalmology 110:665-669, Dec., 1990, "Treatment of Traumatic Optic Neuropathy With Corticosteroids", Thomas C. Spoor, et al.
Arch Ophthal–Vol. 80, Oct. 1968, "Radioactive Depot-Corticosteroid Penetration into Monkey Ocular Tissue", Robert A. Hyndiuk, M.D. et al., pp. 499-503.
Investigative Ophthalmology, vol. 4, No. 3, "An autoradiographic study of the penetration of subconjunctivally injected hydrocortisone into the normal and inflamed rabbit eye", H. J. McCartney, et al., pp. 297-302, (1965).
Am. Journal of Ophthalmology 103:281-288, Mar., 1987, "Echographic Localization of Corticosteroids After Periocular Injection", William R. Freeman, et al.
Arch. Ophthal–vol. 79, Jun. 1968, "Patterns in Experimental Uveitis", Samuel B. Aronson, pp. 763-767.
Ophthalmology, May 1988, vol. 95, No. 5, "Ocular Complications Associated With Retrobulbar Injection", Craig M. Morgan, et al., pp. 660-665.
Am. Journal of Ophthalmology 92:245-251, 1981, "Results with a Temporary Balloon Buckle for the Repair of Retinal Detachment", Harvey Lincoff, et al.
J. of Royal Society of Medicine, vol. 84, 1991, "Prospects for the Treatment of Multiple Sclerosis", Richard A. C. Hughes, pp. 63 and 64.

*Primary Examiner*—Frederick E. Waddell
*Assistant Examiner*—Zohreh A. Fay
*Attorney, Agent, or Firm*—Oliff & Berridge

[57] ABSTRACT

Therapeutic compositions are administered to the ocular tissues by positioning a balloon catheter having an illuminating fiberoptic stylette therein in the retrobulbar or parabulbar space of a patient. After the catheter is properly positioned, the composition is sequentially injected at predetermined intervals over a period of time. A variety of compositions can be administered including corticosteroids, antibiotics, macular degeneration alleviating compositions and inflammation alleviating compositions. Such administration of the therapeutic composition sustains appropriate levels of the composition in the ocular tissues without inducing toxic effects in unaffected tissues.

12 Claims, 6 Drawing Sheets

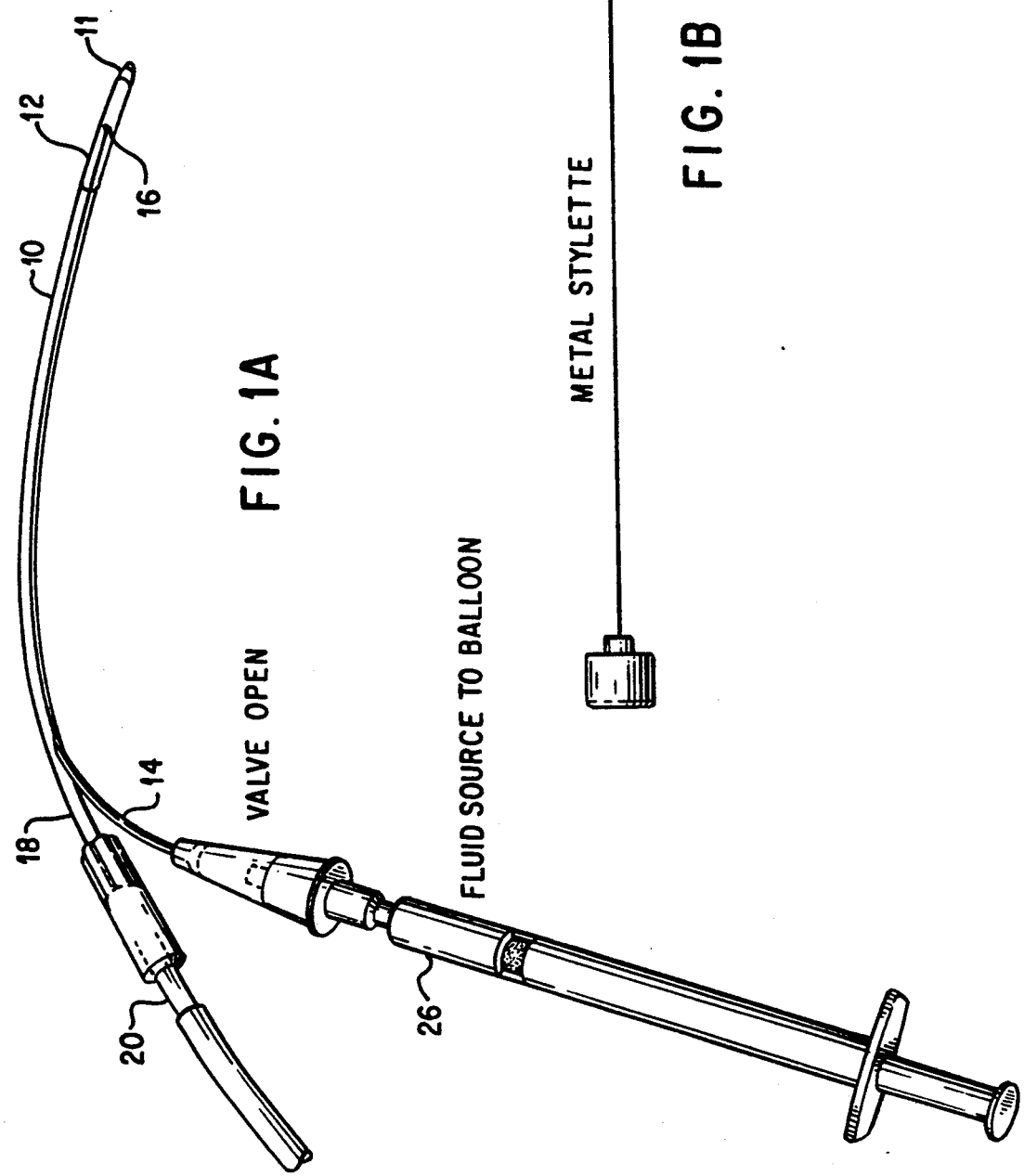

METHOD FOR THE DELIVERY OF COMPOSITIONS TO THE OCULAR TISSUES

BACKGROUND OF THE INVENTION

Field of the Invention

The present invention relates to a method for delivery of compositions to the ocular tissues and, more particularly, to a method for delivering compositions to the ocular tissues in sufficient quantity without toxic effects.

Description of the Related Art

The administration of compositions to the eye and optic nerve has been used in the treatment of a variety of different medical conditions. For example, medications such as corticosteroids have been used to treat multiple sclerosis, optic neuritis (inflammation of the optic nerve) and posterior uveitis (inflammation of the posterior portion of the vascular layer of the eye).

Typically, such medications are systemically administered for penetration into the eye. The penetration, however, is substantially hindered by the bloodretinal barrier. Accordingly, large doses of the medication must be administered in order for therapeutic benefits to be obtained in the portion of the eye to be treated. Furthermore, systemic administration of medications for treatment of such conditions produces numerous side effects and complications, particularly if the medications are administered over a prolonged period of time. Such side effects and complications include rounding and puffiness of the face, chemosis and swelling of the eyelids, obesity, hypertension, hyperlipidemia, hyperglycemia, glycosuria, negative nitrogen balance, muscle weakness, osteoporosis, acne, hirsutism, delayed wound healing, peptic ulcers, bruising of the skin, subconjunctival and retinal hemorrhage, psychoses, increased susceptibility to infections, hypokalemia, hypochloremic alkalosis, sodium retention and edema, thromboembilic phenomena, pseudotumor cerebri with papilledema, loss of libido and amenorrhea. A rapid reduction in the administration of such medications may result in acute adrenocortical insufficiency.

Retrobulbar local administration of medications has been used for the treatment of inflammation of posterior portions of the eye and optic nerve. Such administration delivers a high concentration into the surrounding tissue while minimizing the toxicity encountered in systemic administration. This retrobulbar administration, however, requires repeated injections. As a result of the necessity for repeated injections, further complications arise including retrobulbar hemorrhage, infection and penetration of the globe or optic nerve.

An indwelling catheter has been used to orbitally infuse medications. This catheter is, however, difficult to secure in place. Accordingly, glue or sutures are used therewith, the glue or sutures increasing the risk of infection encountered in using the catheter.

The Lincoff et al article, "A Fiberoptic Stylette for Localizing the Balloon Buckle", describes a fiberoptic balloon catheter for insertion into the parabulbar space. After positioning of the balloon catheter, the balloon is expanded for compression between the eye and the bony orbit and elevation of intraocular pressure. As the eye decompresses, the indentation of the balloon increases and produces a buckle high enough to close a retinal break and cause subretinal fluid to be absorbed. The balloon is correctly placed by the illumination of a fiberoptic stylette positioned in the expanded balloon and monitoring of the catheter tip using an ophthalmoscope. While such a catheter is useful for the temporary retinal buckling procedure, the use of this balloon catheter for the delivery of medications to the ocular tissues is not recognized.

U.S. Pat. No. 3,788,327 to Donowitz et al discloses a surgical implant device including a valve conduit as a means for controlling intra-ocular pressure. The implant device drains excess fluid build-up in the anterior and posterior chambers of the eye, thus relieving the increased pressure. The valve is a one way valve allowing only the drainage of excess fluid and not the administration of a medication.

U.S. Pat. No. 4,820,270 to Hardcastle et al discloses a balloon catheter for passage into a body cavity. The device has a stem portion comprising two concentric tubes being joined at one pair of ends by a flexible member covering the opening of a passage formed between the two tubes. The balloon can be inflated within the body cavity using pressurized fluid supplied thereto. In addition, the device can be used to remove or supply a fluid to the body cavity. The catheter has a central lumen which may contain, e.g., fiberoptics for visualization of the body interior.

U.S. Pat. No. 4,454,151 to Waterbury discloses the use of pyrrolo pyrroles to treat ophthalmic diseases, particularly those diseases associated with inflammation. The compounds can be delivered to the eye topically in the form of an ointment, by subconjunctival injection and by retrobulbar injection. Accordingly, repeated injection of the compounds is required to achieve the desired level of the administered compound, thus increasing the possibility of further complications.

U.S. Pat. No. 4,689,041 to Corday et al discloses a method and apparatus for the delivery of fluids via a catheter inserted into a patient's regional venous system. The catheter has an inflatable balloon on its distal end which maintains the positioning of the catheter while diagnostic agents are administered.

U.S. Pat. No. 3,954,110 to Hutchinson discloses a retention catheter having a balloon enclosing the distal tip and a pair of opposed drainage openings retracted from the distal tip, the openings extending through the balloon into a drainage lumen. Upon inflation of the balloon, the catheter assumes a correct position enabling drainage of a body cavity. The device is not used for the administration of a medication.

While the related art describes devices for delivering medication to the body, the related art does not achieve delivery of sufficiently high levels of a composition to the ocular tissues without producing toxic effects to other organs.

OBJECTS AND SUMMARY OF THE INVENTION

An object of the present invention is to provide a method for administering a sufficient quantity of composition to the ocular tissues.

Another object of the present invention is to administer a composition to the ocular tissues without producing toxic effects on other organs.

A further object of the present invention is to administer a composition to the ocular tissues with a minimum amount of trauma.

To achieve the foregoing and other objects and to overcome the shortcomings discussed above, a method of administering compositions to the ocular tissues is provided which delivers an appropriate level of the composition without producing toxic effects on other organs. A multiple lumen balloon catheter is inserted into the retrobulbar or parabulbar space. The catheter contains a fiberoptic stylette which is illuminated for observation by an ophthalmoscope to ensure proper positioning of the catheter. The balloon is expanded to retain the catheter in its proper position. The composition is sequentially injected at predetermined intervals until a steady state at the desired therapeutic level is obtained.

BRIEF DESCRIPTION OF THE DRAWINGS

The invention will be described in detail with reference to the following drawings in which like reference numerals refer to like elements and wherein:

FIGS. 1A-1C illustrate an embodiment of an apparatus used for composition delivery to the ocular tissues to the ocular tissues;

DETAILED DESCRIPTION OF THE PREFERRED EMBODIMENTS

Figure 1C:
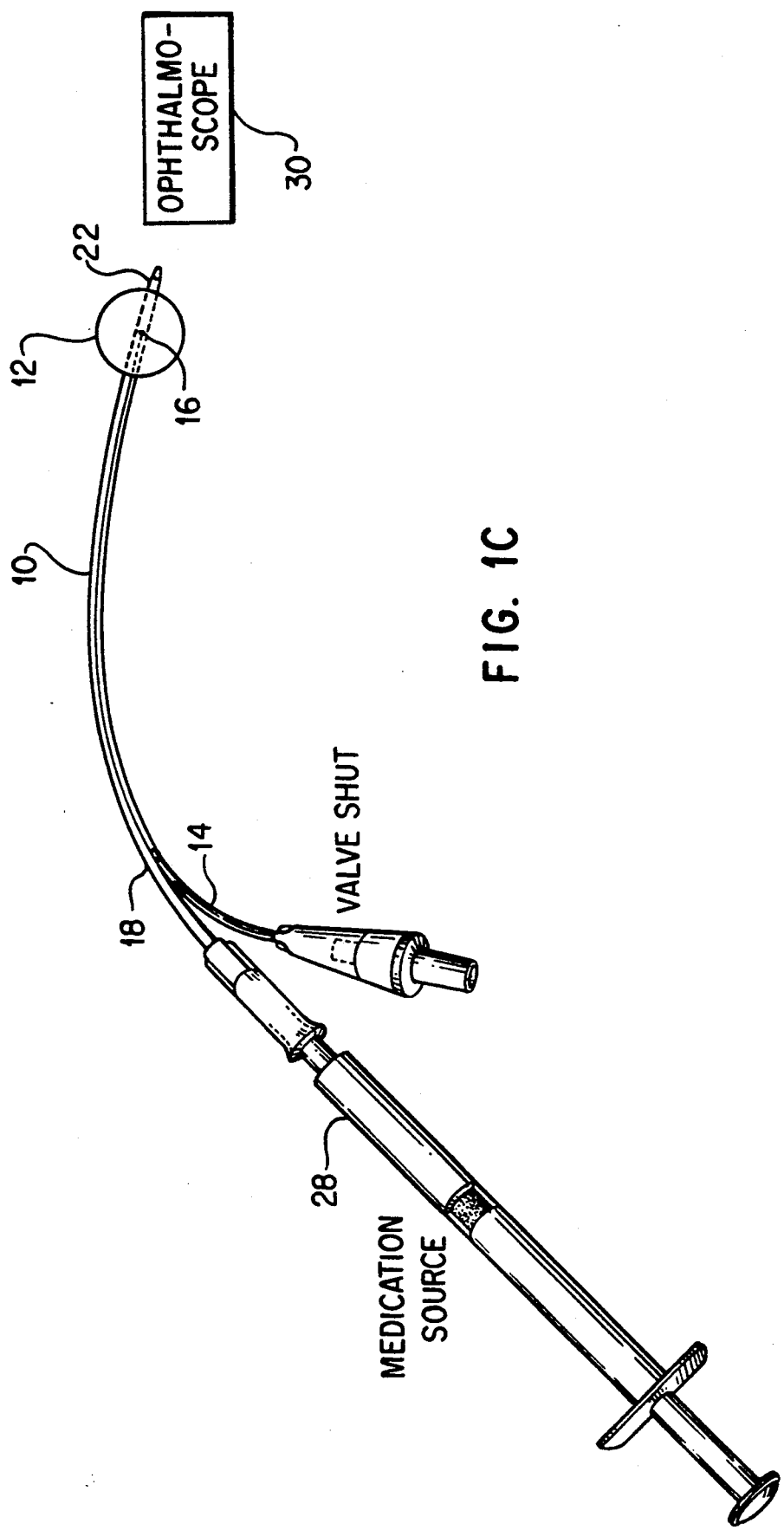

Referring now to the drawings, and particularly to FIGS. 1A-1C thereof, a device used for the delivery of a composition to the ocular tissues is described. Apparatus 1 includes a double lumen catheter 10 having a distal end portion 11 of a blunt, soft, preferably plastic material. Distal end 11 of catheter 10 includes a balloon 12. A fluid source 26 communicates with balloon 12 via a first lumen 14, the fluid source supplying fluid to balloon 12 for expansion thereof. At least one opening 16 is provided in lumen 14 to supply the fluid from fluid source 26 to balloon 12.

Catheter 10 includes a second lumen 18 through which a composition is administered to the retrobulbar or parabulbar space through openings 22. Composition source 28 supplies the composition to lumen 18 for delivery to the retrobulbar or parabulbar space.

A fiberoptic stylette 20 is provided in lumen 18. Illumination of fiberoptic stylette 20 enables observation of the distal end 11 of catheter 10 by an ophthalmoscope 30 as catheter 10 is guided to its proper position in the retrobulbar or parabulbar space. While fiberoptic stylette 20 is shown as being located in lumen 18, alternatively, an additional lumen can be provided in catheter 10 for receipt of fiberoptic stylette 20. In addition, any lumenal configuration can be used such as multiple concentric lumens.

The diameter of catheter 10 preferably approximates 1.9 millimeters to minimize trauma during insertion. Fiberoptic stylette 20 is preferably a 20-gauge plastic fiberoptic.

Apparatus 1 is accurately positioned within the retrobulbar or parabulbar space. After proper positioning, a therapeutic composition is supplied from composition source 28 through lumen 18 and openings 22 into the retrobulbar or parabulbar space. Predetermined amounts of the composition are sequentially injected at predetermined intervals to obtain sufficiently high concentrations of the composition in the ocular tissues without producing toxic effects to other areas.

The following examples illustrate the enhanced effect of administering compositions to the retrobulbar or parabulbar space using apparatus 1.

Experiment

Materials and Methods

Thirty New Zealand Albino rabbits weighing 2.7-3.5 kg were used in this experiment. Each animal was anesthetized with an intramuscular injection of 1 ml of ketamine hydrochloride (100 mg/ml) and 1 ml of xylazine hydrochloride (20 mg/ml). One drop of 1% tropicamide and 1% cyclogel were applied topically to dilate the rabbits' pupils. A pretreatment sample of blood was withdrawn. The left eye of each rabbit was anesthetized with one drop of propracaine hydrochloride. The double lumen fiberoptic parabulbar balloon catheter was placed inferotemporally between the lateral and inferior rectus muscles of the left eye through a 2 mm conjunctival incision at the limbus. The catheter was guided to be placed near the optic nerve visually via an indirect ophthalmoscope. When the balloon was within a half disc diameter from the disc, it was inflated with 0.6 ml of sterile water to secure its position. The portion of the catheter extending beyond the eye was taped to the rabbit's ear.

Twelve rabbits were used to study the concentration of cortisol in ocular tissues following a single injection through the catheter. Fifty milligrams of hydrocortisone sodium succinate (500 mg/4 ml Abott Laboratories, North Chicago, Illinois) were injected through the stylette lumen of the fiberoptic balloon catheter. Post treatment blood samples were withdrawn and the animals were euthanized at 1, 2, 3 and 4 hours after injection. Nine other rabbits were used to study the concentration of cortisol levels in ocular tissues following repeated administration of 50 mg of hydrocortisone sodium succinate. The drug was injected through the balloon catheter two, four and six times at three hour intervals. Post treatment samples of blood were drawn and the animals were euthanised three hours after their last scheduled dose.

One rabbit was used to evaluate the ocular tissue levels produced by an intravenous injection of 50 mg of hydrocortisone sodium succinate, and the eyes were enucleated at 30 minutes and 2 hours post injection. One rabbit was used to assess serum levels at various intervals between 10 minutes and two days after retrobulbar injection of 50 mg hydrocortisone sodium succinate via the balloon catheter. Four other rabbits were used to study the histopathology of the catheterized eye following six injections of 50 mg hydrocortisone sodium succinate at three hour intervals. One of these rabbits was prepared for electron microscopy study.

Specimen Preparation

The pretreatment and post treatment blood samples were centrifuged and the serum obtained for analysis. Both eyes of each animal were enucleated. The adventitial tissue was removed, and the eye was rinsed under a stream of normal saline for twenty seconds. The eye was opened with a circumferential incision 2 mm from the limbus, and the anterior segment was removed. All of the vitreous was separated from the retina. The retina and the choroid were dissected from the scleral shell. The chorioretinal tissue sample was then weighed and placed in a glass tube with 1 ml of methylene dichloride. Similarly, the optic nerve was dissected from the sclera, weighed and placed in 1 ml of methylene dichloride. The optic nerve, chorioretinal and vitreous samples were then homogenized with a tissue tearer for 45 seconds.

Figure 2:
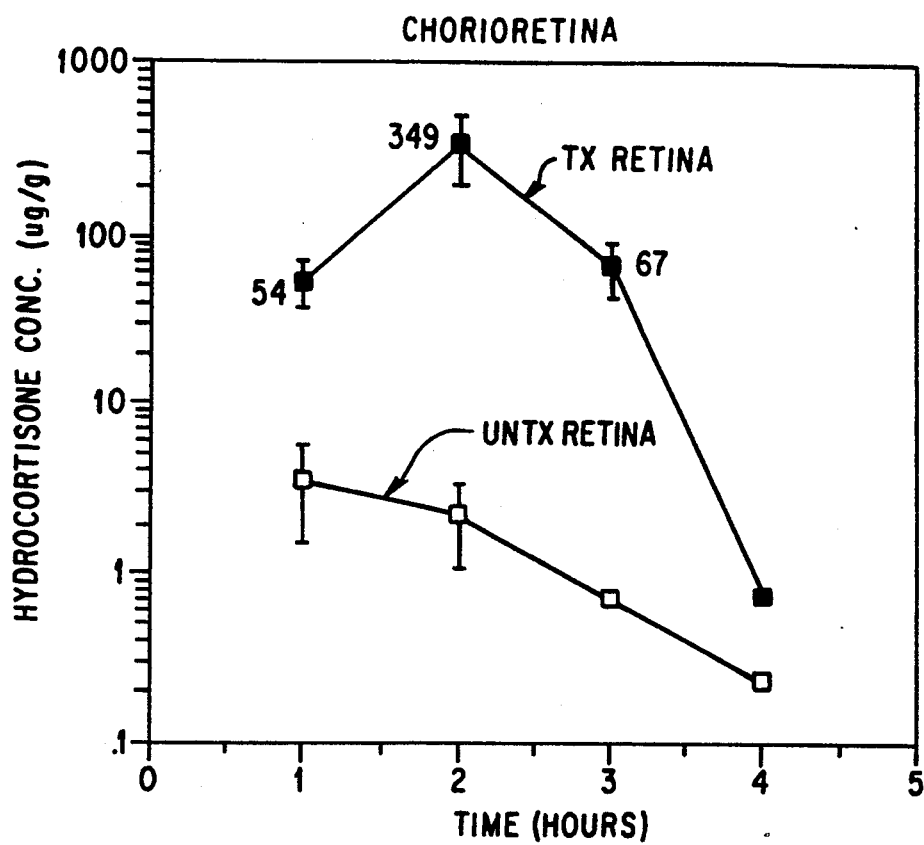
FIG. 2 shows a graph of the hydrocortisone concentration in the chorioretina of a treated and untreated eye.

All samples were then centrifuged at 2,000 RPM for 10 minutes. The supernatant was then analyzed for cortisol by radioimmunoassay capable of detecting 0.01 ug/ml with an accuracy of ±5%.

retina, 80 times greater in the optic nerve, and 20 times greater in the vitreous compared to the fellow eyes. As shown in FIG. 2, the average chorioretinal concentration in the treated eyes was 54.15, 349.11, 67.63 and 0.76 ug/g wet tissue after 1, 2, 3 and 4 hours respectively. These concentrations were much higher than the fellow eye (FIG. 1).

Figure 3:
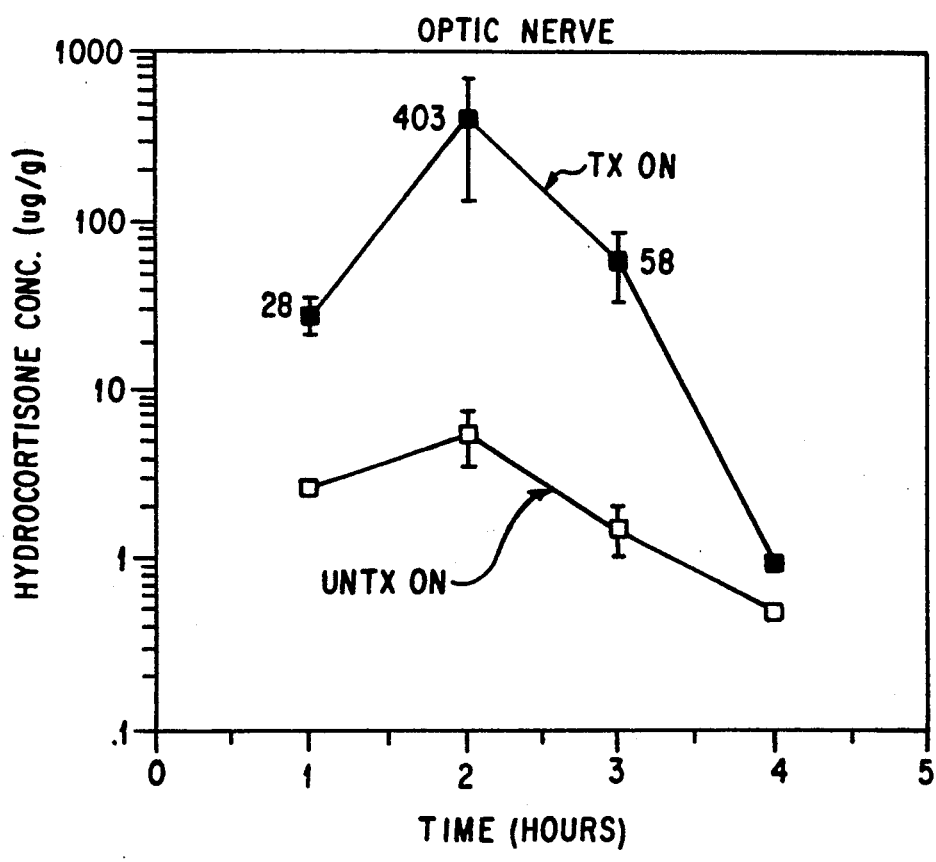
FIG. 3 shows a graph of the hydrocortisone concentration in the optic nerve of a treated and untreated eye.

As shown in FIG. 3, the average concentration of cortisol in the treated optic nerve was 28.08, 403.61, 58.71 and 0.98 ug/ml after 1, 2, 3 and 4 hours respectively. These levels were much higher than the levels attained in the fellow optic nerve.

Figure 4:
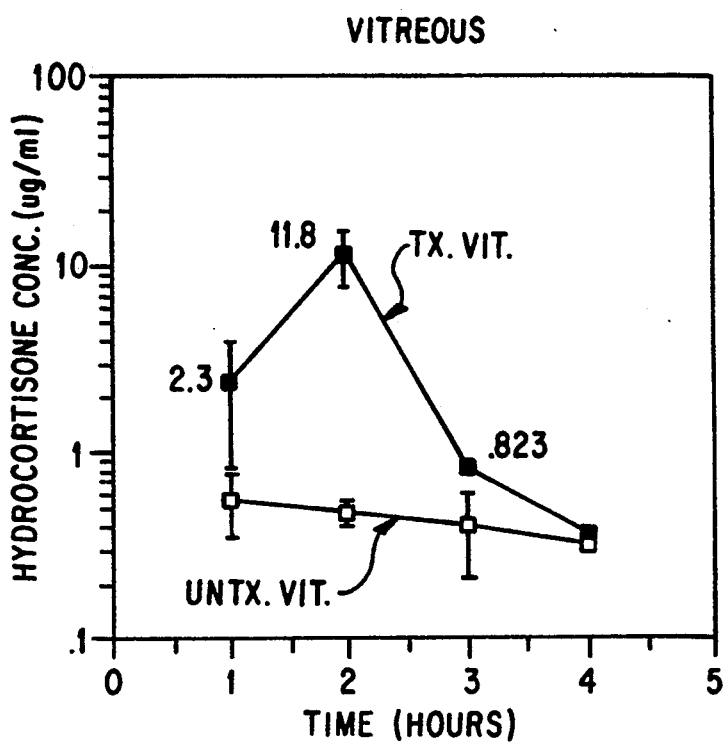
FIG. 4 shows a graph of the hydrocortisone concentration in the vitreous of a treated and untreated eye.

As shown in FIG. 4, the average concentration of cortisol in the vitreous was 2.38, 11.48, 0.82 and 0.24 ug/ml after 1, 2, 3 and 4 hours respectively which was higher than the vitreous levels in the fellow eye.

Figure 5:
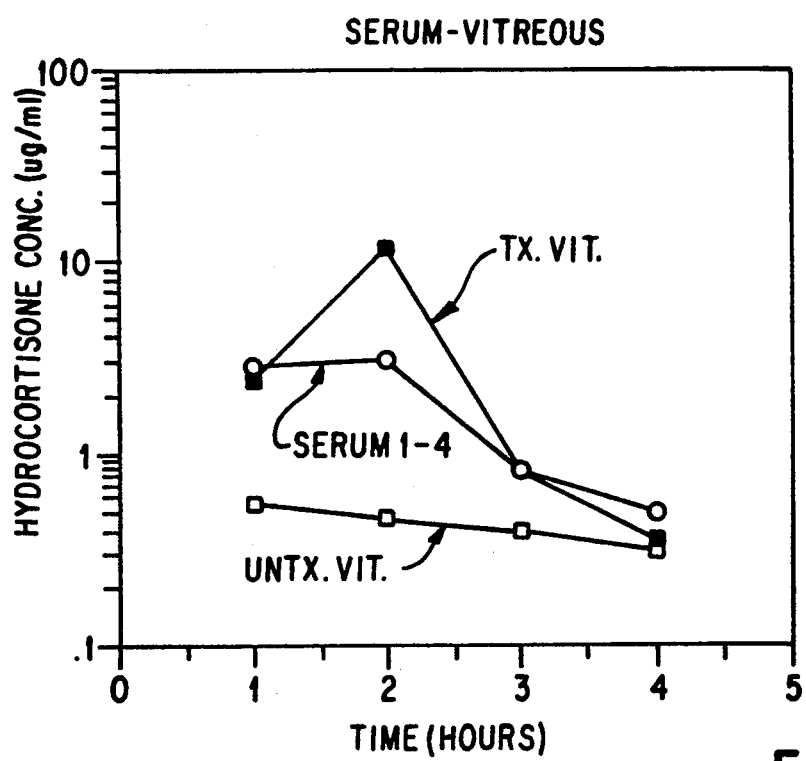
FIG. 5 shows a comparative graph of the hydrocortisone concentration in the serum.

As shown in FIG. 5, the average cortisol level in the serum was 2.85, 3.09, 0.82 and 0.5 ug/ml at 1,2,3 and 4 hours respectively which was comparable to ocular tissue levels in the fellow eye.

Concentrations in the optic nerve, retina, vitreous and serum are tabulated in Table 1 below for each animal.

TABLE 1

Experiment 1, Part A- Bioassay of Hydrocortisone Sodium Succinate After Single Dose of 50 mg Given Retrobulbarly in the Left Eye via the balloon catheter.

| Time | Rabbit No. | Serum ug/ml | Left Eye | | | Right Eye | | |
|---|---|---|---|---|---|---|---|---|
| | | | Chorio-Retina ug/g | Optic Nerve ug/g | Vitreous Humor ug/ml | Chorio-Retina ug/g | Optic Nerve ug/g | Vitreous Humor ug/ml |
| 1 hr. | 1 | 1.83 | 66.279 | 31.25 | 3.78 | 1.836 | 1.649 | .308 |
| | 2 | 3.2 | 61.29 | 20.205 | 2.77 | 5.82 | 1.645 | .680 |
| | 3 | 3.53 | 34.89 | 32.773 | 0.59 | 2.97 | 4.65 | .700 |
| | Avg | 2.853 | 54.153 | 28.079 | 2.38 | 3.542 | 2.648 | .562 |
| 2 hr. | 1 | 1.94 | 184.783 | 139.216 | .7 | 1.327 | 4.827 | .494 |
| | 2 | 3.16 | 380.41 | 387.80 | 13.4 | 3.48 | 7.826 | .508 |
| | 3 | 3.16 | 482.14 | 683.809 | 14.04 | 1.84 | 4.01 | .402 |
| | Avg | 3.086 | 349.11 | 403.608 | 11.48 | 2.215 | 5.554 | .468 |
| 3 hr. | 1 | .89 | 45.098 | 86.111 | .86 | .474 | .7097 | .228 |
| | 2 | .8 | 92.754 | 55.593 | .85 | 1.009 | 1.5 | .332 |
| | 3 | .78 | 65.04 | 34.44 | .76 | .6745 | 2.368 | .64 |
| | Avg | .823 | 67.631 | 58.71 | .823 | .719 | 1.529 | .400 |
| 4 hr. | 1 | .570 | 0.555 | 0.606 | .358 | .464 | .588 | .346 |
| | 2 | .220 | 0.91 | 1.8 | .340 | .125 | .596 | .294 |
| | 3 | .72 | 0.819 | .522 | .375 | .1241 | .305 | .303 |
| | Avg | .503 | 0.761 | .976 | .357 | .238 | .496 | .314 |

Results

Figure 6:
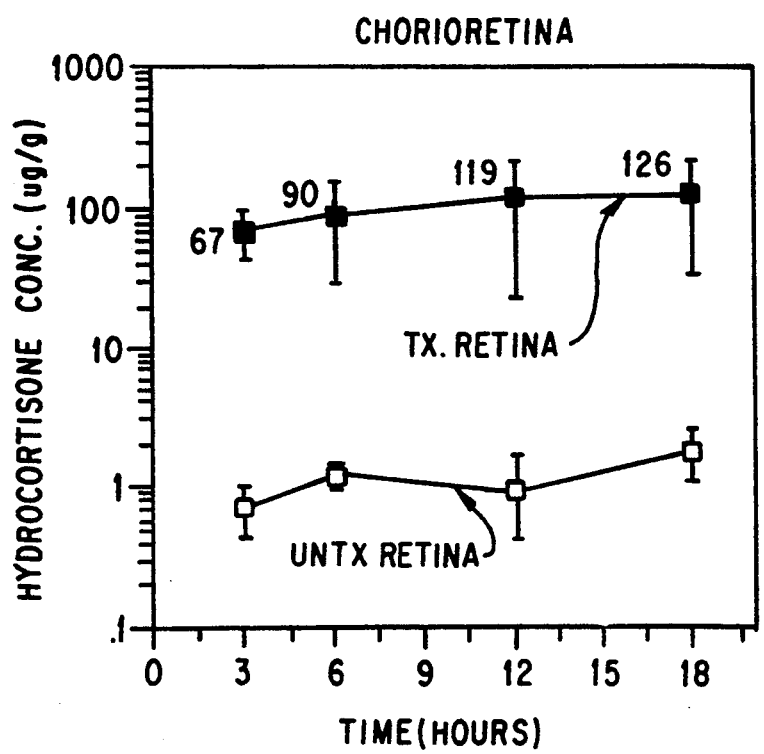
FIG. 6 shows a graph of hydrocortisone concentration in the chorioretina after repeated injections.
Figure 7:
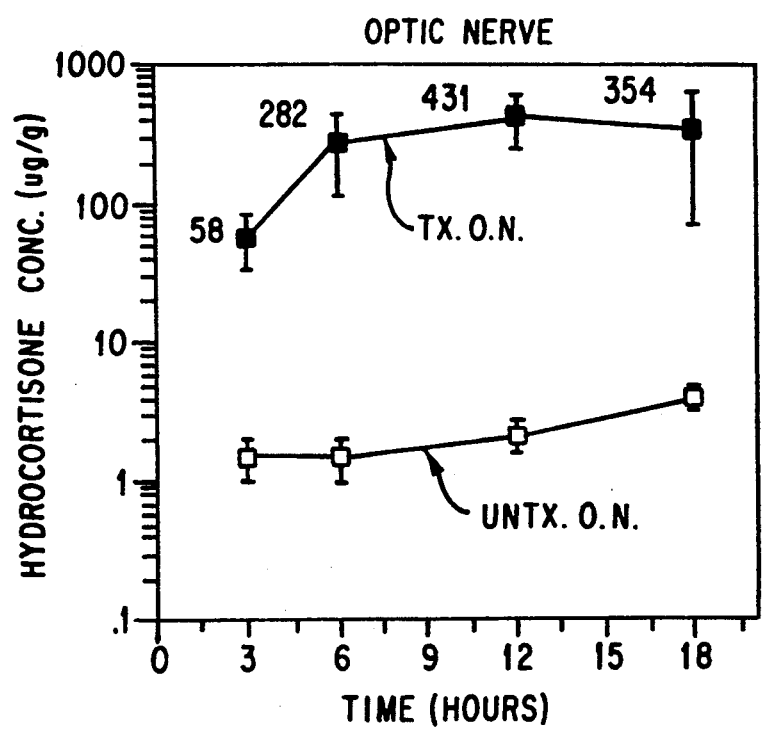
FIG. 7 shows a graph of hydrocortisone concentrations in the optic nerve after repeated injections.

The concentrations of cortisol (hydrocortisone) in the optic nerve, choroid-retina and vitreous in the catheterized eyes reached their peak levels at two hours after a single injection. The ocular tissue levels subsequently declined to approximate the serum level 4 hours after the single injection. Peak cortisol levels in the catheterized eyes were 120 times greater in the choroid- The half life of cortisol in ocular tissues was calculated and the schedule for repeated injection was made every three hours with the aim of achieving a steady state in the trough level of the curve. With repeated injections, the concentration of cortisol in the choroidretina and optic nerve achieved a steady state level as shown in Table 2 below and illustrated in FIGS. 6 and 7.

TABLE 2

Experiment 2, Part A- Bioassay of Hydrocortisone Sodium Succinate After Repeated Administration of 50 mg Given Retrobulbarly in the Left Eye via the balloon catheter at 3 hr. intervals.

| Injection | Rabbit No. | Serum ug/ml | Left Eye | | | Right Eye | | |
|---|---|---|---|---|---|---|---|---|
| | | | Chorio-Retina ug/g | Optic Nerve ug/g | Vitreous Humor ug/ml | Chorio-Retina ug/g | Optic Nerve ug/g | Vitreous Humor ug/ml |
| 2. | 1 | 1.44 | 159.574 | 445.454 | 5.54 | 1.205 | 1.829 | .366 |
| | 2 | 1.41 | 42.22 | 110.52 | 1.8 | .996 | .939 | .864 |
| | 3 | 0.83 | 70 | 292.92 | 8.84 | 1.387 | 1.792 | .370 |
| | Avg | 1.226 | 90.598 | 282.964 | 5.39 | 1.196 | 1.52 | .533 |
| 4 | 1 | 1.73 | 48.83 | 231.578 | 4.2 | 1.094 | 2.227 | 1.44 |
| | 2 | 0.5 | 80.292 | 519.355 | 12 | 0.391 | 1.147 | 0.24 |
| | 3 | 1.06 | 229.911 | 543.75 | 24.4 | 1.452 | 3.448 | 0.38 |
| | Avg | 1.09 | 119.68 | 431.558 | 13.533 | 0.979 | 2.274 | .686 |

TABLE 2-continued

Experiment 2, Part A- Bioassay of Hydrocortisone Sodium Succinate After Repeated Administration of 50 mg Given Retrobulbarly in the Left Eye via the balloon catheter at 3 hr. intervals.

| Injection | Rabbit No. | Serum ug/ml | Left Eye | | | Right Eye | | |
|---|---|---|---|---|---|---|---|---|
| | | | Chorio-Retina ug/g | Optic Nerve ug/g | Vitreous Humor ug/ml | Chorio-Retina ug/g | Optic Nerve ug/g | Vitreous Humor ug/ml |
| 6 | 1 | 1.87 | 229.76 | 140.64 | 33.3 | 2.13 | 2.524 | .96 |
| | 2 | 0.85 | 52.72 | 250.33 | 15.92 | 2.207 | 2.69 | .816 |
| | 3 | 0.73 | 96.977 | 674 | 17.88 | 1.009 | 7.44 | .502 |
| | Avg | 1.15 | 126.486 | 354.99 | 22.366 | 1.782 | 4.218 | .759 |

Figure 8:
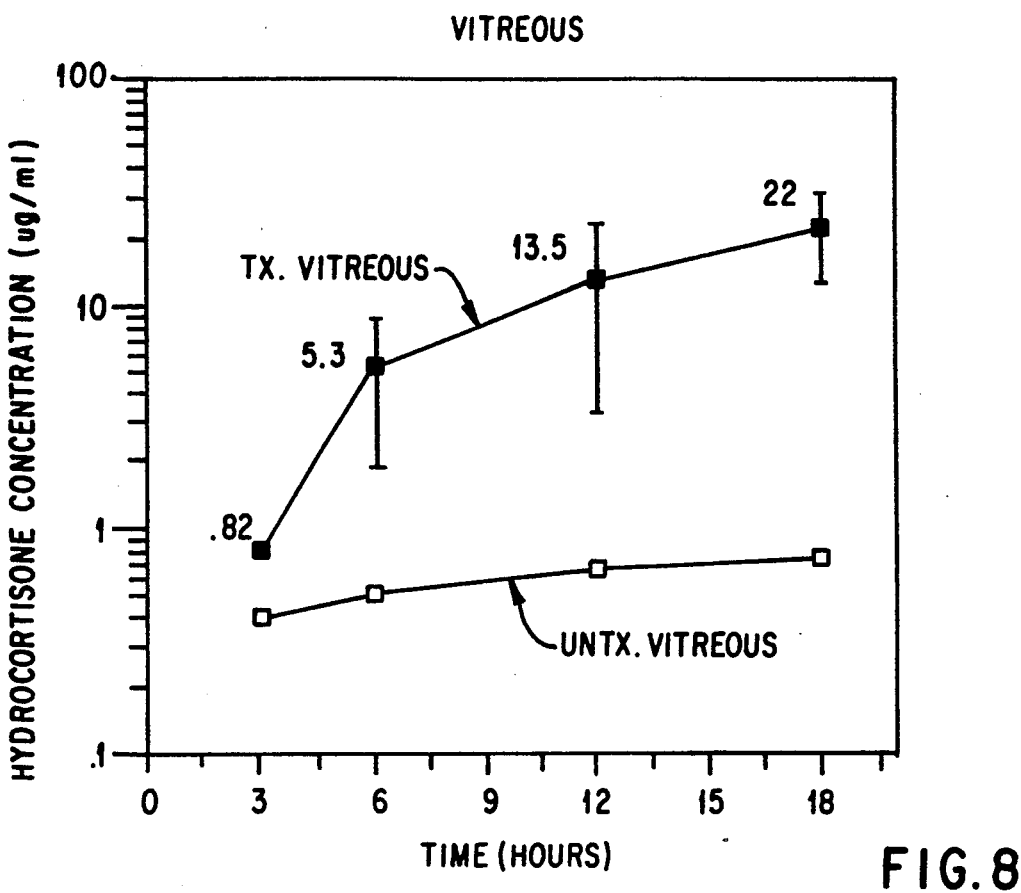
FIG. 8 shows a graph of hydrocortisone concentration in the vitreous after repeated injections.

The levels in the vitreous continued to rise as shown in FIG. 8.

Figure 9:
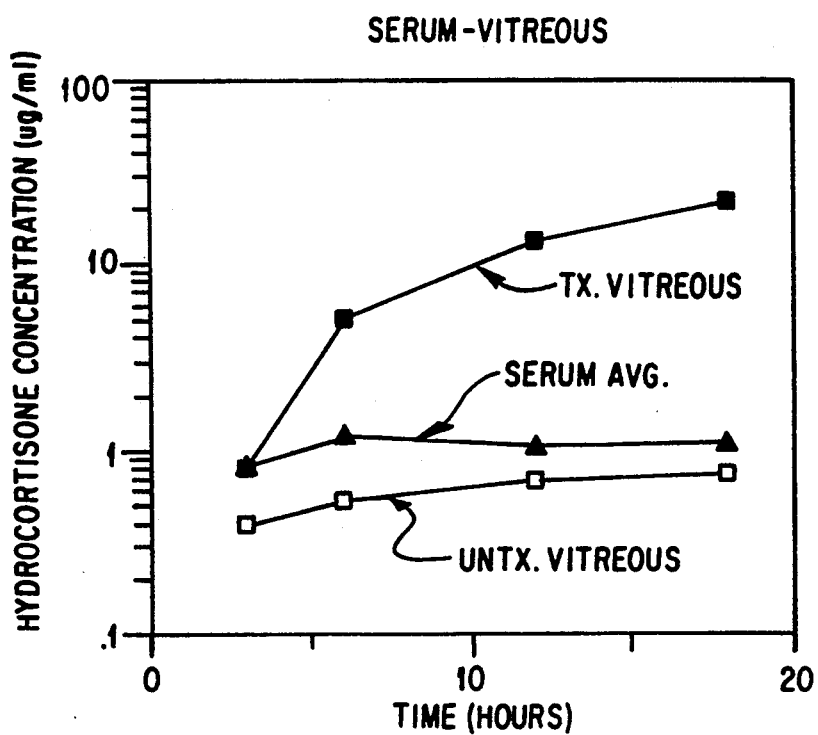
FIG. 9 shows a comparative graph of hydrocortisone concentration in the serum after repeated injections.

Intravenous injection of 50 mg of hydrocortisone sodium succinate produced ocular tissue levels comparable to that of the fellow eyes of the rabbits treated with the parabulbar balloon catheter. As illustrated in FIG. 9, peak serum levels of cortisol after intravenous injection were 8 times greater than the peak serum levels after hydrocortisone administration via the parabulbar balloon catheter.

In the above described experiment, the administration of compounds to the ocular tissues achieves a higher concentration of the composition in the intended area without adversely affecting other body tissues and organs. Apparatus 1 enables administration of the composition over an extended period of time so that the level of the composition can be sustained. Furthermore, the patient is not exposed to the hazardous effects and complications associated with repeated retrobulbar injections such as perforation of the globe, intraocular injection, optic nerve meninges injection with resulting central nervous system complications and injection into the choroidal or retinal vasculature. Since distal end 11 of catheter 10 is formed as a blunt, soft plastic material, puncture and hemorrhage is inhibited.

Because catheter 10 is positioned adjacent the intended area and the amount of the composition administered by source 28 is readily determined, the dose of composition administered can be accurately titrated according to the patient's clinical response.

While the above-described experiment involved the administration of corticosteroid material, it is readily apparent that various compositions can be administered using apparatus 1. For example, an antibiotic such as clindamycin can be administered to treat ocular lesions such as toxoplasma choroiditis. Other antibiotics such as vancomycin, garamycin, tetracycline and sulfonamides can be administered to treat bacterial endophthalmitis. Compositions can be introduced directly beneath the macula to alleviate the progression of age related macular degeneration. For example, a tissue plasminogen activator can be infused to dissolve the subretinal hemorrhage associated with degenerative maculopathy.

While this invention has been described in conjunction with a specific embodiment thereof, it is evident that many alternatives, modifications and variations will be apparent to those skilled in the art. Accordingly, the preferred embodiment of the invention as set forth herein is intended to be illustrative, not limiting. Various changes may be made without departing from the spirit and scope of the invention as defined in the following claims.

What is claimed is:

1. A method for administering a composition to the ocular tissues, comprising:
   positioning a balloon catheter in the retrobulbar space by expanding the balloon to maintain the position of the catheter in the retrobulbar space; and
   sequentially injecting through the catheter a predetermined amount of the composition at predetermined intervals.

2. The method according to claim 1, wherein said catheter includes an illuminating fiberoptic stylette and said positioning includes guiding said catheter into the retrobulbar space by observing said catheter using an ophthalmoscope.

3. The method according to claim 1, wherein the composition is a corticosteroid.

4. The method according to claim 1, wherein the composition is an antibiotic.

5. The method according to claim 1, wherein the composition alleviates macular degeneration.

6. The method according to claim 1, wherein the composition alleviates inflammation.

7. A method for administering a composition to the ocular tissues, comprising:
   positioning a balloon catheter in the parabulbar space by expanding the balloon to maintain the position of the catheter in the parabulbar space; and
   sequentially injecting through the catheter a predetermined amount of the composition at predetermined intervals.

8. The method according to claim 7, wherein said catheter includes an illuminating fiberoptic stylette and said positioning includes guiding said catheter into the parabulbar space by observing said catheter using an ophthalmoscope.

9. The method according to claim 7, wherein the composition is a corticosteriod.

10. The method according to claim 7, wherein the composition is an antibiotic.

11. The method according to claim 7, wherein the composition alleviates macular degeneration.

12. The method according to claim 7, wherein the composition alleviates inflammation.

* * * * *